US005712142A

United States Patent [19]

Adney et al.

[11] Patent Number: 5,712,142
[45] Date of Patent: Jan. 27, 1998

[54] METHOD FOR INCREASING THERMOSTABILITY IN CELLULASE ENNZYMES

[75] Inventors: William S. Adney, Golden; Steven R. Thomas, Denver; John O. Baker, Golden; Michael E. Himmel, Littleton; Yat-Chen Chou, Wheat Ridge, all of Colo.

[73] Assignee: Midwest Research Institute, Kansas City, Mo.

[21] Appl. No.: 604,913

[22] Filed: Feb. 22, 1996

Related U.S. Application Data

[63] Continuation-in-part of Ser. No. 276,213, Jul. 15, 1994, Pat. No. 5,536,655, which is a continuation-in-part of Ser. No. 125,115, Sep. 21, 1993, Pat. No. 5,366,884, which is a continuation-in-part of Ser. No. 826,089, Jan. 27, 1992, Pat. No. 5,275,944, which is a continuation-in-part of Ser. No. 412,434, Sep. 26, 1989, Pat. No. 5,110,735.

[51] Int. Cl.$^6$ .................. C12N 9/42; C12N 1/20; C12P 21/06; C17H 21/04
[52] U.S. Cl. .......... 435/209; 435/69.1; 435/252.3; 435/252.33; 435/320.1; 536/23.1; 536/23.2; 536/23.7
[58] Field of Search ................. 435/209, 69.1, 435/252.3, 252.31, 252.33, 253.5, 254.21, 320.1; 536/22.1, 23.1, 23.2, 23.7

[56] References Cited

U.S. PATENT DOCUMENTS

| | | | |
|---|---|---|---|
| 5,110,735 | 5/1992 | Tucker et al. | 435/209 |
| 5,275,944 | 1/1994 | Himmel et al. | 435/209 |
| 5,366,884 | 11/1994 | Adney et al. | 435/209 |
| 5,432,075 | 7/1995 | Himmel et al. | 435/209 |
| 5,536,655 | 7/1996 | Thomas et al. | 435/209 |

OTHER PUBLICATIONS

Mohagheghi et al., *Int. J. System. Bacteriol.*, 36:435-443 (1986).

Lejeune et al., *Biosynthesis and Biodegradation of Cellulose*, C. Haigler and P.J. Weimer, Ed., Marcel-Dekker, NY 1991, pp. 623-672.

*Primary Examiner*—Rebecca E. Prouty
*Assistant Examiner*—Tekchand Saidha
*Attorney, Agent, or Firm*—Edna M. O'Connor; Ken Richardson; Ruth Eure

[57] ABSTRACT

The gene encoding *Acidothermus cellulolyticus* E1 endoglucanase is cloned and expressed in *Pichia pastoris*. A new modified E1 endoglucanase enzyme comprising the catalytic domain of the full size E1 enzyme demonstrates enhanced thermostability and is produced by two methods. The first method of producing the new modified E1 is proteolytic cleavage to remove the cellulose binding domain and linker peptide of the full size E1. The second method of producing the new modified E1 is genetic truncation of the gene encoding the full size E1 so that the catalytic domain is expressed in the expression product.

13 Claims, 8 Drawing Sheets

| | | | | |
|---|---|---|---|---|
| AGGGYWHTSG | REILDANNVP | VRIAGINWFG | FETCNYVVHG | LWSRDYRSML | 50
| DQIKSLGYNT | IRLPYSDDIL | KPGTMPNSIN | FYQMNQDLQG | LTSLQVMDKI | 100
| VAYAGQIGLR | IILDRHRPDC | SGQSALWYTS | SVSEATWISD | LQALAQRYKG | 150
| NPTVVGFDLH | NEPHDPACWG | CGDPSIDWRL | AAERAGNAVL | SVNPNLLIFV | 200
| EGVQSYNGDS | YWWGGNLQGA | GQYPVVLNVP | NRLVYSAHDY | ATSVYPQTWF | 250
| SDPTFPNNMP | GIWNKNWGYL | FNQNIAPVWL | GEFGTTLQST | TDQTWLKTLV | 300
| QYLRPTAQYG | ADSFQWTFWS | WNPDSGDTGG | ILKDDWQTVD | TVKDGVLAPI | 350
| KSSIFDPV | | | | | 358

Fig. 5

```
GGATCCACGT TGTACAAGGT CACCTGTCCG TCGTTCTGGT AGAGCGGCGG GATGGTCACC         60
CGCACGATCT CTCCTTTGTT GATGTCGACG GTCACGTGGT TACGGTTTGC CTCGGCCGCG        120
ATTTTCGCGC TCGGGCTTGC TCCGGCTGTC GGGTTCGGTT TGGCGTGGTG TGCGGAGCAC        180
GCCGAGGCGA TCCCAATGAG GGCAAGGGCA AGAGCGGAGC CGATGGCACG TCGGGTGGCC        240
GATGGGGTAC GCCGATGGGG CGTGGCGTCC CCGCCGCGGA CAGAACCGGA TGCGGAATAG        300
GTCACGGTGC GACATGTTGC CGTACCGCGG ACCCGGATGA CAAGGGTGGG TGCGCGGGTC        360
GCCTGTGAGC TGCCGGCTGG CGTCTGGATC ATGGGAACGA TCCCACCATT CCCCGCAATC        420
GACGCGATCG GGAGCAGGGC GGCGCGAGCC GGACCGTGTG GTCGAGCCGG ACGATTCGCC        480
CATACGGTGC TGCAATGCCC AGCGCCATGT TGTCAATCCG CCAAATGCAG CAATGCACAC        540
ATGGACAGGG ATTGTGACTC TGAGTAATGA TTGGATTGCC TTCTTGCCGC CTACGCGTTA        600
CGCAGAGTAG GCGACTGTAT GCGGTAGGTT GGCGCTCCAG CCGTGGGCTG GACATGCCTG        660
CTGCGAACTC TTGACACGTC TGGTTGAACG CGCAATACTC CCAACACCGA TGGGATCGTT        720
CCCATAAGTT TCCGTCTCAC AACAGAATCG GTGCGCCCTC ATGATCAACG TGAAAGGAGT        780
ACGGGGAGA ACAGACGGGG GAGAAACCAA CGGGGGATTG GCGGTGCCGC GCGCATTGCG        840
GCGAGTGCCT GGCTCGCGGG TGATGCTGCG GGTCGGCGTC GTCGTCGCGG TGCTGGCATT        900
GGTTGCCGCA CTCGCCAACC TAGCCGTGCC GCGGCCGGCT CGCGCCGCGG GCGGCGGCTA        960
TTGGCACACG AGCGGCCGGG AGATCCTGGA CGCGAACAAC GTGCCGGTAC GGATCGCCGG       1020
CATCAACTGG TTTGGGTTCG AAACCTGCAA TTACGTCGTG CACGGTCTCT GGTCACGCGA       1080
CTACCGCAGC ATGCTCGACC AGATAAAGTC GCTCGGCTAC AACACAATCC GGCTGCCGTA       1140
CTCTGACGAC ATTCTCAAGC CGGGCACCAT GCCGAACAGC ATCAATTTTT ACCAGATGAA       1200
TCAGGACCTG CAGGGTCTGA CGTCCTTGCA GGTCATGGAC AAAATCGTCG CGTACGCCGG       1260
TCAGATCGGC CTGCGCATCA TTCTTGACCG CCACCGACCG GATTGCAGCG GCAGTCGGC        1320
GCTGTGGTAC ACGAGCAGCG TCTCGGAGGC TACGTGGATT CCGACCTGC AAGCGCTGGC        1380
GCAGCGCTAC AAGGGAAACC CGACGGTCGT CGGCTTTGAC TTGCACAACG AGCCGCATGA       1440
CCCGGCCTGC TGGGGCTGCG GCGATCCGAG CATCGACTGG CGATTGGCCG CCGAGCGGGC       1500
CGGAAACGCC GTGCTCTCGG TGAATCCGAA CCTGCTCATT TTCGTCGAAG GTGTGCAGAG       1560
CTACAACGGA GACTCCTACT GGTGGGGCGG CAACCTGCAA GGAGCCGGCC AGTACCCGGT       1620
CGTGCTGAAC GTGCCGAACC GCCTGGTGTA CTCGGCGCAC GACTACGCGA CGAGCGTCTA       1680
CCCGCAGACG TGGTTCAGCG ATCCGACCTT CCCCAACAAC ATGCCCGGCA TCTGGAACAA       1740
GAACTGGGGA TACCTCTTCA ATCAGAACAT TGCACCGGTA TGGCTGGGCG AATTCGGTAC       1800
GACACTGCAA TCCACGACCG ACCAGACGTG GCTGAAGACG CTCGTCCAGT ACCTACGGCC       1860
GACCGCGCAA TACGGTGCGG ACAGCTTCCA GTGGACCTTC TGGTCCTGGA ACCCCGATTC       1920
CGGCGACACA GGAGGAATTC TCAAGGATGA CTGGCAGACG GTCGACACAG TAAAAGACGG       1980
CTATCTCGCG CCGATCAAGT CGTCGATTTT CGATCCTGTC TAATGATCTG CATCGCCTAG       2040
CAGTCAACCG TCCCCGTCGG TGTCGCCGTC TCCGTCGCCG AGCCCGTCGG CGAGTCGGAC       2100
GCCGACGCCT ACTCCGACGC CGACAGCCAG CCCGACGCCA ACGCTGACCC CTACTGCTAC       2160
GCCCACGCCC ACGGCAAGCC CGACGCCGTC ACCGACGGCA GCCTCCGGAG CCCGCTGCAC       2220
CGCGAGTTAC CAGGTCAACA GCGATTGGGG CAATGGCTTC ACGGTAACGG TGGCCGTGAC       2280
AAATTCCGGA TCC                                                          2293
```

Fig. 6

METHOD FOR INCREASING THERMOSTABILITY IN CELLULASE ENNZYMES

This application is a continuation-in-part of Ser. No. 08/276,213, filed Jul. 15, 1994, now U.S. Pat. No. 5,536,655, which is a continuation-in-part of Ser. No. 08/125,115, filed Sep. 21, 1993, now U.S. Pat. No. 5,366,884, which is a continuation-in-part of Ser. No. 07/826,089, filed Jan. 27, 1992, now U.S. Pat. No. 5,275,944, which was a continuation-in-part of Ser. No. 412,434, filed Sep. 26, 1989 now U.S. Pat. No. 5,110,735.

The United States Government has rights in this invention under Contract No. DE-AC36-83CH10093 between the United States Department of Energy and the National Renewable Energy Laboratory, a Division of the Midwest Research Institute.

FIELD OF THE INVENTION

The invention relates to methods for increasing the thermostability of cellulose enzymes.

BACKGROUND OF THE INVENTION

The development of an economic process for the conversion of low-value biomass to useful products via fermentation requires the optimization of several key steps, including cellulase production and performance. Practical utilization of cellulose by hydrolysis with cellulase to produce glucose requires large amounts of cellulase to fully depolymerize cellulose. For example, about one kilogram cellulase preparation may be used for every fifty kilograms of cellulose. Economical production of cellulose is also compounded by the relatively slow growth rates of cellulase-producing fungi and the long times required for cellulose induction. Therefore, improvements in or alternative cellulase production systems capable of greater productivities of cellulase activity than may be possible from currently available systems would significantly reduce the cost of cellulose hydrolysis and make the large-scale bioconversion of cellulosic biomass more economical.

Highly thermostable cellulose enzymes are secreted by the cellulolytic thermophile *Acidothermus cellulolyticus* gen. nov., sp. nov. These are discussed in U.S. Pat. Nos. 5,110,735, 5,275,944, 5,366,884, and 5,432,075. All four of these patents are included herein in their entirety by this reference thereto. This bacterium was originally isolated from decaying wood in an acidic, thermal pool at Yellowstone National Park and deposited with the American Type Culture Collection (ATCC) under collection number 43068 (Mohagheghi et al. 1986. *Int. J. System. Bacteriol.* 36:435–443).

The cellulase complex produced by this organism is known to contain several different cellulase enzymes with maximal activities at temperatures of 75° C. to 83° C. These cellulases are resistant to inhibition from cellobiose, an end product of the reactions catalyzed by cellulase. Also, the cellulases from *Acidothermus cellulolyticus* are active over a broad pH range centered about pH 6. A high molecular weight cellulase isolated from growth broths of *Acidothermus cellulolyticus* was found to have a molecular weight of approximately 156,600 to 203,400 daltons by sodium dodecyl sulfate polyacrylamide gel electrophoresis (SDS-PAGE). This enzyme is described in U.S. Pat. No. 5,110,735.

A novel cellulase enzyme, known as the E1 endoglucanase, also secreted by *Acidothermus cellulolyticus* into the growth medium, is described in detail in U.S. Pat. No. 5,275,944. In its native form, this endoglucanase demonstrates a temperature optimum of 83° C. and a specific activity of 40 µmole glucose release from carboxymethylcellulose/min/mg protein. This E1 endoglucanase was further identified as having an isoelectric pH of 6.7. It is this E1 endoglucanase which has been modified and made the subject of this patent application. The E1 endoglucanase is a multidomain cellulase having a catalytic domain and a cellulose binding domain connected to the catalytic domain by a linker peptide.

SUMMARY OF THE INVENTION

The E1 endoglucanase described above, has been modified to increase its thermostability. The present modification has increased the thermostability of this enzyme by effectively doubling the length of time which this enzyme demonstrates half-maximal activity at elevated temperatures, as well as increasing the temperature at which maximal rates of catalysis are observed. The modification comprises eliminating the cellulose binding domain and linker peptide of the enzyme from the catalytic domain. It is the catalytic domain containing the catalytically active portion of the molecule, which remains after elimination of the cellulose binding domain and linker peptide, which demonstrates these improved thermal properties. This modification has been accomplished by two methods. The first method for eliminating the cellulose binding domain and linker peptide is by subjecting the entire molecule to proteolytic cleavage, which removes the cellulose binding domain and linker peptide from the catalytic domain. The second method for removing the cellulose binding domain and linker peptide from full size E1 involves modification of the gene which encodes full size E1 so that the cellulose binding domain and linker peptide are not present in the expression product. The E1 enzyme of the present invention which demonstrates enhanced thermostability by elimination of the cellulose binding domain and linker peptide is referred to as "modified", "truncated", "catalytic domain", or "E1 CAT". Also, E1 CAT produced by proteolytic cleavage may be referred to as pE1 CAT and E1 CAT produced by genetic transformation may be referred to as gel CAT.

In addition to the modified E1 endoglucanase having improved thermostability, this invention teaches the expression of full size E1 in a yeast It is therefore an object of the present invention to transform and express the full size E1 endoglucanase gene in a yeast under the same and/or a different gene regulatory system.

It is an object of the present invention to modify the gene encoding the E1 endoglucanase from *Acidothermus cellulolyticus* to enhance its thermostability by eliminating expression of the cellulose binding domain and linker peptide in the gene product.

It is an object of the present invention to provide the DNA sequence which encodes the modified form of the E1 endoglucanase from *Acidothermus cellulolyticus*.

It is another object of the present invention to provide the amino acid sequence of the modified form of the E1 endoglucanase from *Acidothermus cellulolyticus*.

It is another object of the present invention to provide a method for proteolytic cleavage of the cellulose binding domain and linker peptide from the E1 endoglucanase.

It is a further object of the present invention to prepare modified E1 endoglucanases which have different properties from the natural enzyme.

The present invention describes the gene for and the nucleotide sequence of the segment of *Acidothermus cellu-*

*lolyticus* DNA encoding the catalytic domain of the E1 endoglucanase gene. This 2293 base fragment of DNA is unique in nature and discretely defined. The natural gene contains a promoter, a ribosome binding site, a signal peptide, an open reading frame, a termination codon and a putative transcriptional terminator. The modified gene contains a promoter, a ribosome binding site, a signal peptide and one or more termination codons inserted at the C terminus of the catalytic domain.

The cloned gene may also be expressed in other microorganisms under its natural promotor or another promotor recognized by the host microorganism. The cloned gene may be expressed in mammalian systems, higher plants or viral vectors. Alternatively, additional copies of the gene may be introduced into *Acidothermus cellulolyticus* or other heterologous host organism to enhance expression of the enzyme. Additionally, DNA encoding one or more domains of the *Acidothermus cellulolyticus* E1 endoglucanase may be ligated to domains in other compatible endoglucanases to make a recombinant DNA capable of expressing a hybrid endoglucanase enzyme having beneficial properties from both endoglucanases.

BRIEF DESCRIPTION OF THE DRAWINGS

FIG. 5 shows the amino acid translation of the coding sequence of E1 CAT.

FIG. 6 shows the 2293 base pair nucleotide sequence of the region of *Acidothermus cellulolyticus* genomic DNA which contains the modified E1 endoglucanase gene which expresses only the catalytic domain of the enzyme, without the linker peptide or cellulose binding domain.

DETAILED DESCRIPTION OF THE PREFERRED EMBODIMENTS

Figure 1:
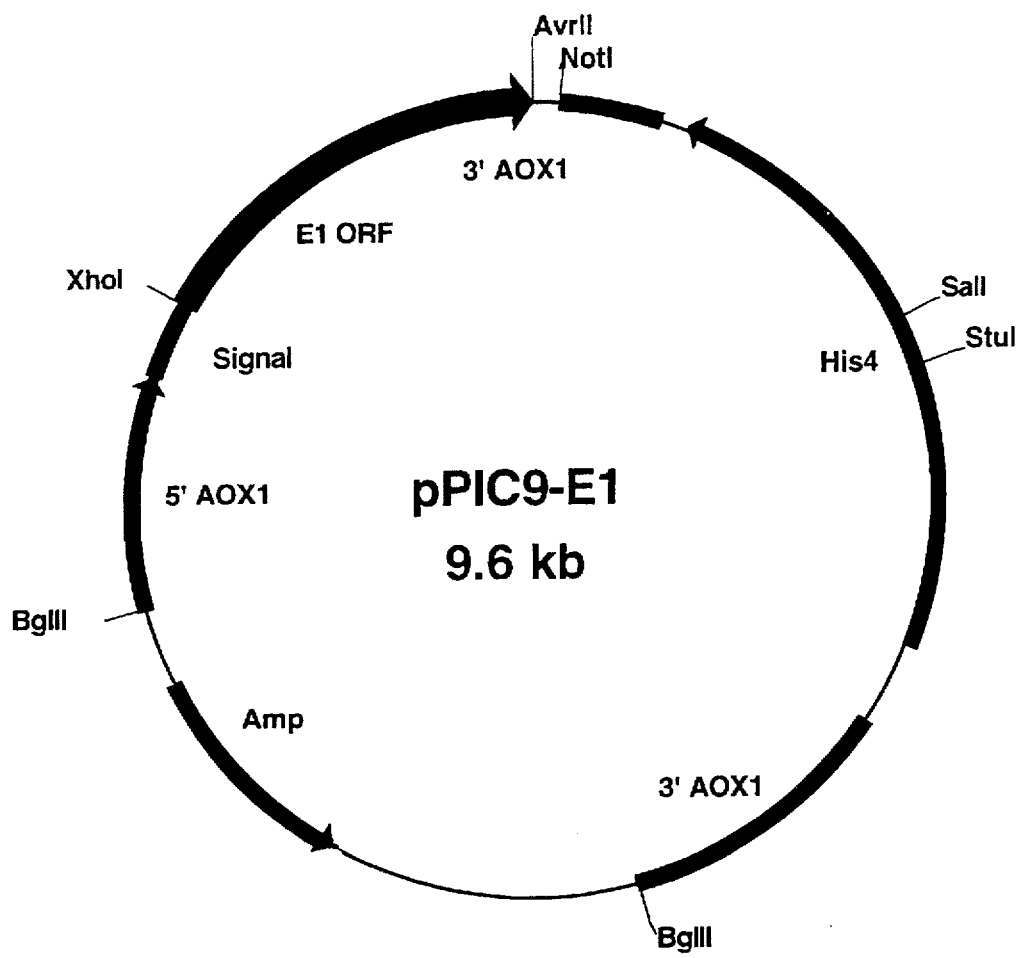
FIG. 1 is a plasmid map of pPIC9-E1.

According to the present invention the entire E1 coding sequence for *Acidothermus cellulolyticus* E1 endoglucanase is cloned and expressed in a different microbial host than is described in the parent to this application, Ser. No. 08/276,213, filed Jul. 15, 1994, which is incorporated herein in its entirety by this reference thereto. The enzyme described in Ser. No. 08/276,213 is a β-1,4 endoglucanase which can hydrolyze cellulose or carboxymethylcellulose and is hereafter referred to as E1 endoglucanase or full size E1. The result is a vastly improved rate of E1 enzyme production over native or genetically engineered bacterial systems, thereby lowering the cost of cellulase. The instant application teaches expression of full size E1 in a yeast, namely *Pichia pastoris*.

Expression of Full Size E1 and Modified E1

For expressing the E1 endoglucanase gene, either the full size E1 gene or the modified E1 gene, one may use a variety of hosts including most bacteria, yeast, fungi, algae, viruses, plants and animals. Organisms which naturally produce cellulase enzymes are preferred host cells along with easy to grow host cells and host cells known to express and secrete heterologous genes in large quantities.

If the host cell is a bacterium, generally a bacterial promoter and regulatory system will be used. For a typical bacterium such as *E. coli*, representative examples of well known promoters include, for example, trc, lac, tac, trp, bacteriophage lambda $P_L$, T7 RNA polymerase promoter, etc. When the expression system is yeast, examples of well known promoters include, but are not limited to GAL 1/GAL 10, alcohol dehydrogenase (ADH), alcohol oxidase (AOX), his3, cycl, etc. For eukaryotic hosts, enhancers such as the yeast Ty enhancer, may be used.

Alternatively, if one wished for the full size or modified E1 endoglucanase gene to be expressed at only a particular time, such as after the culture or host organism has reached maturity, an externally regulated, environmentally-responsive promoter is particularly useful. Examples include those based upon the nutritional or chemical composition of the medium (e.g. methanol, lac, trp, his), temperature regulation (e.g. temperature sensitive regulatory elements), heat shock promoters (e.g. HSP80A, U.S. Pat. No. 5,187,267), stress response (e.g. plant EF1A promoter, U.S. Pat. No. 5,177,011) and chemically inducible promoters (e.g. tetracycline inducible promoter or salicylate inducible promoter U.S. Pat. No. 5,057,422).

Other suitable hosts for expressing full size or modified E1 endoglucanase include members of the genera: Trichoderma, Fusarium, Penicillium, Bacillus, Xanthomonas, Streptomyces, Aspergillus and Pichia, for example. Some of these microorganisms also serve as sources of endoglucanase genes for the formation of mixed domain genes for the production of hybrid enzymes.

Expression of the full size E1 endoglucanase gene has been demonstrated in *E. coli*, *Pichia pastoris* and in *Streptomyces lividans*.

Expressing full size or modified E1 endoglucanase in *E. coli* may be performed under control of a T7 bacteriophage promoter or other promotor recognizable by *E. coli*. Expression of full size E1 in *E. coli* has been enhanced considerably relative to the native gene with the constructs of the present invention. Expression of the full size E1 endoglucanase coding sequence in *S. lividans* has been achieved twice more with several different constructs employing two different promoters. These are the tipA promoter (thiostrepton-inducible) and the ST I-II promoter isolated from a trypsin inhibitor gene from *Streptomyces longisporus*. Expression levels of active, full size, secreted E1 endoglucanase up to 20 mg/L have been achieved with the ST I-II promoter.

Expression of the full size or modified E1 endoglucanase coding sequence in the filamentous fungi, *Aspergillus niger*, *A. awamori*, *A. oryzae*, *A. terreus* and/or *A. nidulans* and *Trichoderma reesei* is achievable using various promoters derived from Aspergillus or Trichoderma. These promoters include, but are not limited to, G3PDH (glyceraldehyde-3-phosphate dehydrogenase), glucoamylase, β-tubulin and IPNS (isopenicillin N synthase) from Aspergillus and CBH I (cellobiohydrolase I), alcohol dehydrogenase, triosephosphate isomerase and α-amylase from *T. reesei*.

The *Acidothermus cellulolyticus* full size E1 endoglucanase gene was cloned, as described in Ser. No. 08/276,213, and expressed in *Pichia pastoris* using the AOX1 promoter and 3' sequences. This expression is taught in Example 1.

EXAMPLE 1

Expression of the Entire Full Size E1 Gene in *Pichia pastoris*

Expression of active E1 endoglucanase in the range of 0.75–1.5 g/L has been accomplished in the yeast, *Pichia*

*pastoris*, by splicing the methanol-inducible alcohol oxidase (AOX1) promoter, including the signal sequence from the *P. pastoris* alcohol oxidase polypeptide to the mature coding sequence of the E1 endoglucanase gene.

*P. pastoris* has been shown to be a useful host organism for expression of large quantities of diverse heterologous proteins. *P. pastoris* was used to express large quantities of active full size E1.

Plasmid 4-5, a pGEM-7 (Promega Corp.) derivative carrying a 3.7 kb genomic fragment of *Acidothermus cellulolyticus* DNA and harboring the entire E1 gene, was used as a template in PCR reactions to amplify the E1 coding sequence for subsequent cloning into the Pichia secretion vector, pPIC9. The primer annealing to the non-coding strand of the template, "E1-f", is a 30-mer with 18 bases of homology to the template, beginning at the mature N-terminus of the E1 polypeptide. The segment of E1-f which is not homologous to the template molecules incorporates 4 codons which encode the C-terminal 4 amino acids of the αF signal peptide which is present in pPIC9 and also includes an XhoI site at the 5' end for use in subsequent cloning into pPIC9. The primer annealing to the coding strand and priming synthesis of the non-coding strand, "E1-r", is a 24-mer with 18 bases of homology to the template. The sequence of E1-r corresponds to the last 5 codons of the E1 coding sequence and the stop codon. The non-homologous 5' tail of E1-r adds an AvrII restriction site for use in subsequent cloning into pPIC9.

E1 on Western blots. Some of the reactive material on these blots runs as two diffuse high molecular weight bands. This material may be heavily glycosylated relative to the main band on the blots, which runs at a molecular weight only slightly higher than native E1 (75–80 kDa vs. 72 kDa). Most of the E1 produced in these cultures was secreted into the medium, as intended. The activity of the E1 secreted into the medium was demonstrated by the ability of these crude culture filtrates to hydrolyze 4-methylumbelliferyl-β-D-cellobioside (MUC), whereas control culture supernatants did not hydrolyze MUC.

Fed-batch fermentations of one of the Pichia transformants were conducted over a period of 4 days. Cultures were grown to a high optical density on 4% glycerol (w/v). When glycerol was exhausted (approx. 30 hours), methanol was fed as the sole carbon source over a period of 66 additional hours. After purification of the E1 from a portion of this culture, the yield was estimated at 1.5 g/L.

The present invention also comprises a further improvement of the E1 enzyme by modification of the physical structure of the enzyme to enhance its thermostable properties. At 80° C., the modified enzyme of the present invention demonstrates increased stability relative to the parent, full size E1, as well as an approximately 10° C. increase in its optimal temperature for activity.

This enhancement is brought about by the cleavage of the cellulose binding domain from the catalytic domain of the full size E1 enzyme. The cleavage of the cellulose binding

```
              signal cleavage site
       XhoI         |
E1-f:  5'-CTC GAG  AAA AGA GCG GGC GGC GGC TAT TGG-3'   (SEQ ID NO: 1)
AA seq     L   E   K   R   A   G   G   G   Y   W       (SEQ ID NO: 2)

AvrII
E1r:   5'-CCT AGG  TTA ACT TGC TGC GCA GGC-3'           (SEQ ID NO: 3)
AA seq     stop    S   A   A   C   A                   (SEQ ID NO: 4)
```

Cloning of the E1 expression construct in pPIC9 was accomplished using the Pichia Expression Kit supplied by Invitrogen (San Diego, Calif.). All procedures are those recommended by Invitrogen. The PCR reaction produces a 1584 bp fragment containing the entire open reading frame for the full size, mature E1 polypeptide. The PCR product was cloned directly into the TA vector, PCRII (Invitrogen, San Diego, Calif.). A single clone containing the PCR product was digested with XhoI and AvrII and the resulting 1.6 kb fragment was cloned into the same sites of pPIC9 to produce pPIC9-E1, which is diagrammatically represented in FIG. 1. Several independent pPIC9-E1 isolates were screened for the existence of XhoI and AvrII sites and subsequently subjected to DNA sequencing across the signal peptide/E1 fusion junction to verify the correct sequence context in this region.

The pPIC9-E1 plasmid was linearized at the unique StuI site and transformed into spheroplasts of *P. pastoris* strain GS115. His⁺ transformants were selected for the Mut⁻ phenotype. Twenty independent His⁺Mut⁻ isolates were screened by PCR using the AOX1 primers. Clones which displayed a 1.8 kb PCR product were screened for expression of E1 endoglucanase activity after growth on methanol.

The media and intracellular contents of cells from cultures grown in the presence of methanol for two days were screened by Western blot analysis using a monoclonal antibody specific for the E1 endoglucanase. All *P. pastoris* clones containing the foreign DNA were shown to express domain from the catalytic domain can be accomplished by more than one method. The first method of cleaving the cellulose binding domain from the catalytic domain is the enzymatic cleavage of the cellulose binding domain from the full-sized E1. This is taught in Example 2.

EXAMPLE 2

Method for the Production, Purification and Papain Cleavage of Full Size E1 Endoglucanase to Produce E1 CAT.

Full size E1 enzyme was recombinantly produced using *S. lividans* strain TK24 expressing E1-pIJ702 grown in 30 g/L Tryptic Soy Broth (Difco) with 5 ug/mL thiostrepton using a New Brunswick Microferm fermenter. The fermentation broth (10 L) was harvested using a CEPA continuous flow centrifuge, the supernatant concentrated and diafiltered against 20 mM Bis-Tris, pH 5.8 to a final volume of 300 mL using an Amicon CH2 concentrator and 10,000 MW cutoff hollow-fiber cartridges. Yields of native 72 kDa molecular weight E1 from these fermentations ranged from 1.2 to 2 mg/L, as estimated from purification yields.

The recombinant full size enzyme was purified with essentially a three step purification process consisting of hydrophobic interaction chromatography (HIC) followed by anion exchange and finally, size exclusion chromatography. The HIC step employed a column packed with 250 mL of Pharmacia Fast Flow Phenyl Sepharose. This was followed by anion-exchange chromatography using a 6 mL Pharmacia Resource Q anion exchange column.

For the hydrophobic interaction step, ammonium sulfate was added to the concentrated culture supernatant of one 10 L fermentation to a final concentration 0.5M. A total volume of 300 mL of this concentrate was loaded onto the phenyl sepharose column and washed extensively with 20 mM Tris, 0.5M $(NH_4)_2SO_4$ pH 8.0. The column was developed with a linear decreasing gradient (0.5M–zero) of $(NH_4)_2SO_4$. Recombinant full size E1 eluted at zero salt concentration. Fractions containing E1 activity were identified using 4-methylumbelliferyl β-D-cellobioside (MUG) assays. Active fractions were combined, concentrated and diafiltered against 20 mM Tris pH 8.0, after which they were loaded directly onto the anion-exchange column and eluted with a increasing NaCl gradient (0–300 mM). A final buffer exchange and purification step was done using size exclusion chromatography with a 2.6 cm×10 cm Pharmacia Superdex 200 column and using one of two buffer systems; either 20 mM acetate, 100 mM NaCl, pH 5.0 buffer or 50 mM ammonium acetate, pH 6.2 buffer depending upon the eventual use of the enzyme.

The E1 catalytic domain was produced by proteolytic cleavage with papain. The proteolytic digestions were done in 50 mM ammonium acetate, pH 6.2 buffer. Molar ratios of 72 kDa MW E1/23 kDa MW papain cleaved E1 of 6/1 were used. Papain digestions were incubated at 28° C. for 24 h. The catalytic domain was separated from full size recombinant E1, E1-CBD (cellulose binding domain), linker peptides and papain by SEC using a 2.6 cm×10 cm Pharmacia Superdex 200 column.

Figure 4:
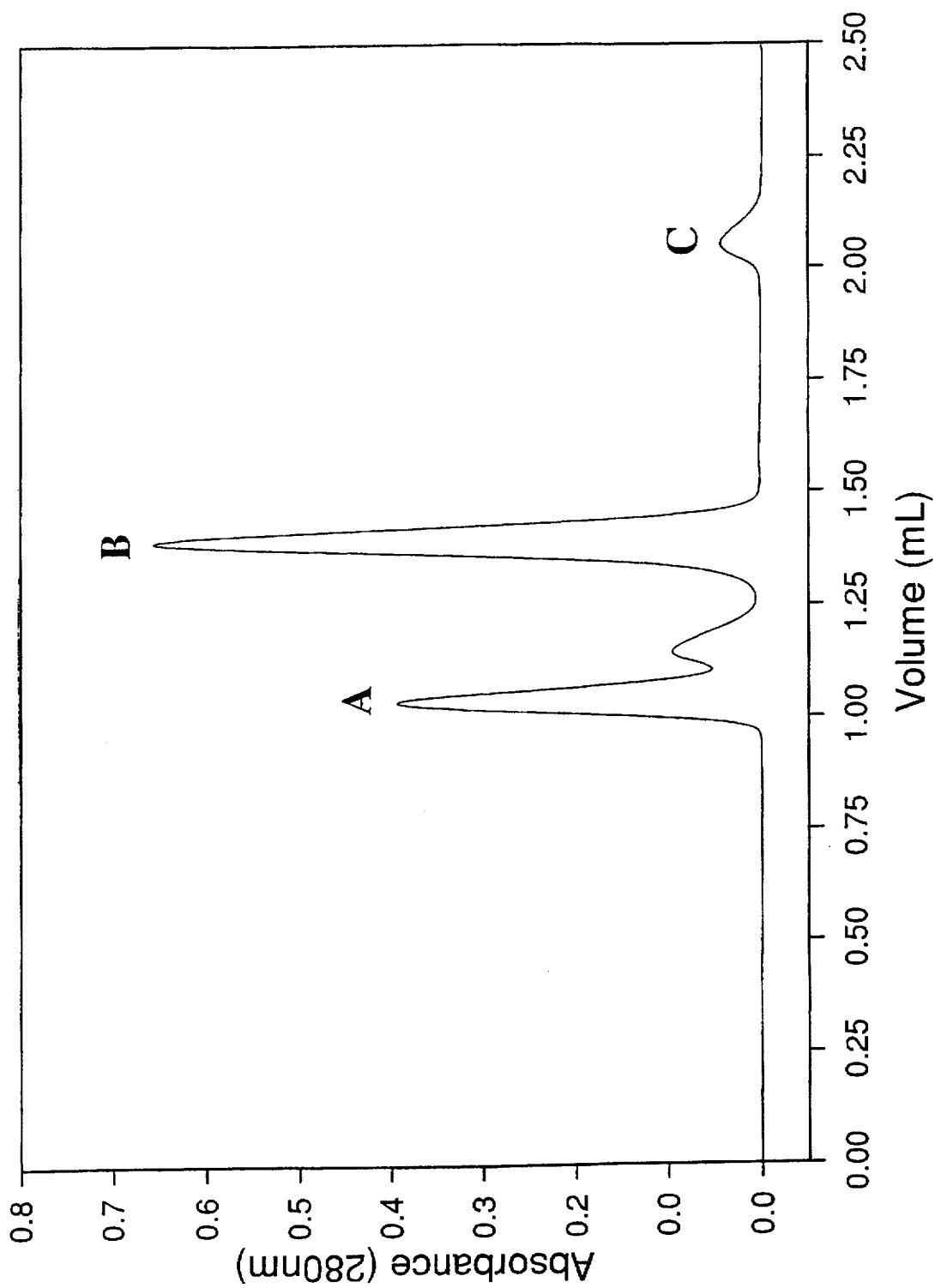
FIG. 4 is a chromatogram showing purified constituent domains of full size E1 by size exclusion chromatography.

A chromatogram demonstrating the purification of modified catalytic domain from papain cleaved S. lividans recombinant E1 by size exclusion chromatography is shown in FIG. 4. Peak A is unmodified full size E1 enzyme, peak B is the catalytic domain, and peak C is the cellulose binding domain of the cleaved product. Also, peak B reacts with a monoclonal antibody (MAB) specific for full size E1, thereby confirming that this fragment contains epitopes for which this MAB shows specificity.

In order to confirm the identity of the peptide isolated from the papain digestion, the peak B peptide was subjected to analytical ultracentrifugation using a Beckman Optima XLa centrifuge. Sedimentation equilibrium analysis yielded an estimated molecular weight of 41,600 daltons for this peptide. SDS-PAGE analysis rendered a molecular weight estimate of 42,000 daltons. These values compare well with the calculated molecular weight predicted from amino acid sequence for the catalytic domain (i.e., 40,192 da.) Due to the limits of detection of the techniques utilized herein, these molecular weight values are well within the range of experimental error and therefore the molecular weight of the E1 CAT is in the range of about 40,000 to 42,000 Daltons.

Figure 2:
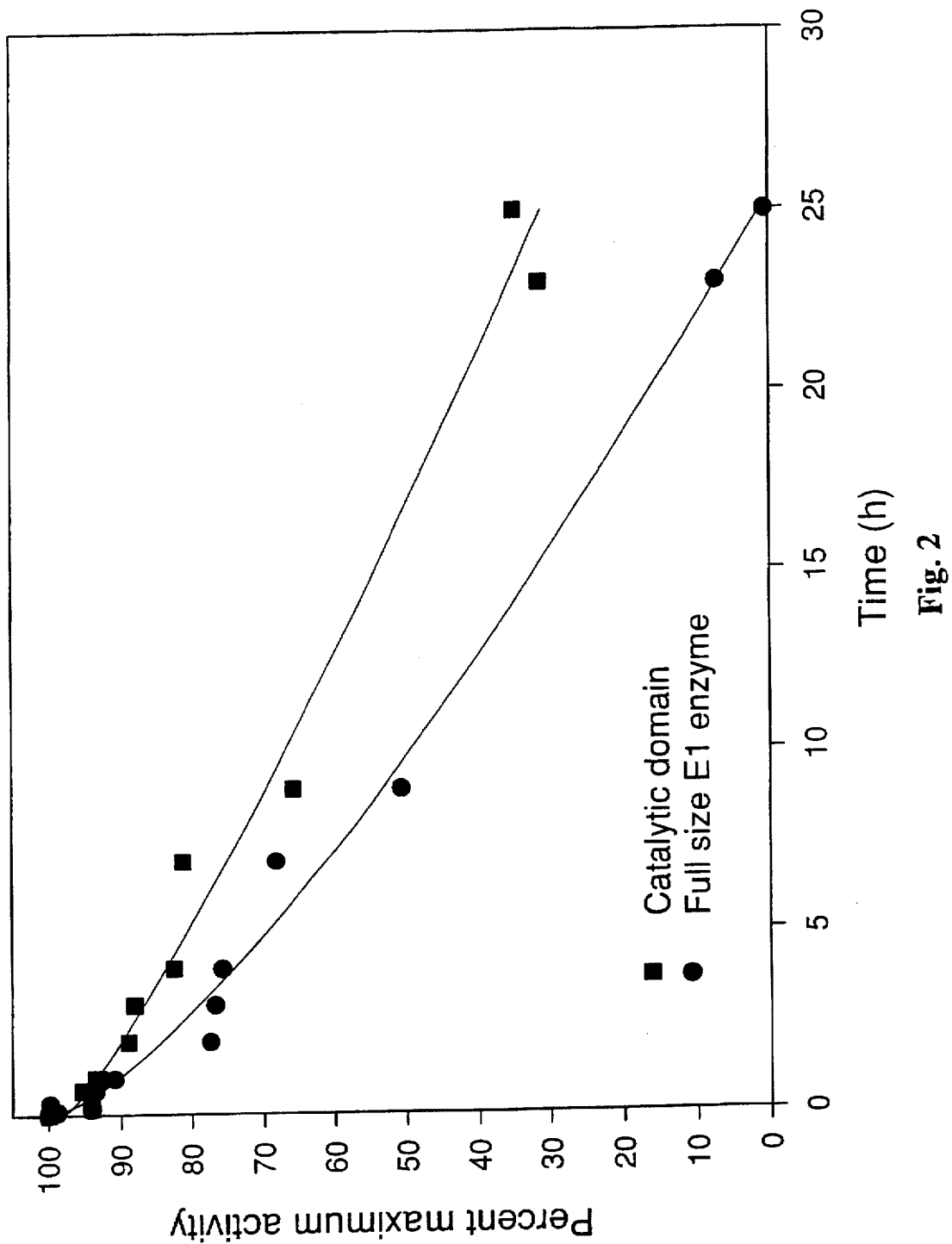
FIG. 2 compares the functional half-life of the full size E1 enzyme to the functional half-life of the catalytic domain of the E1 enzyme at 80° C.

Comparison of the thermal stability at 80° C. of pE1 CAT and full size E1 endoglucanase, both produced from a Streptomyces host, can be seen in FIG. 2. The enzyme was incubated at 80° C. in 20 mM acetate, 100 mM NaCl, pH 5.0 buffer with timed aliquots removed, and each assayed for activity using 1 mg/mL p-nitrophenyl-β-D-cellobioside substrate in 20 mM acetate, 100 mM NaCl, pH 5.0, at 65° C. for 30 minutes. Activity values are expressed as a percentage of the activity detected at time zero (e.g., 100%).

Figure 3:
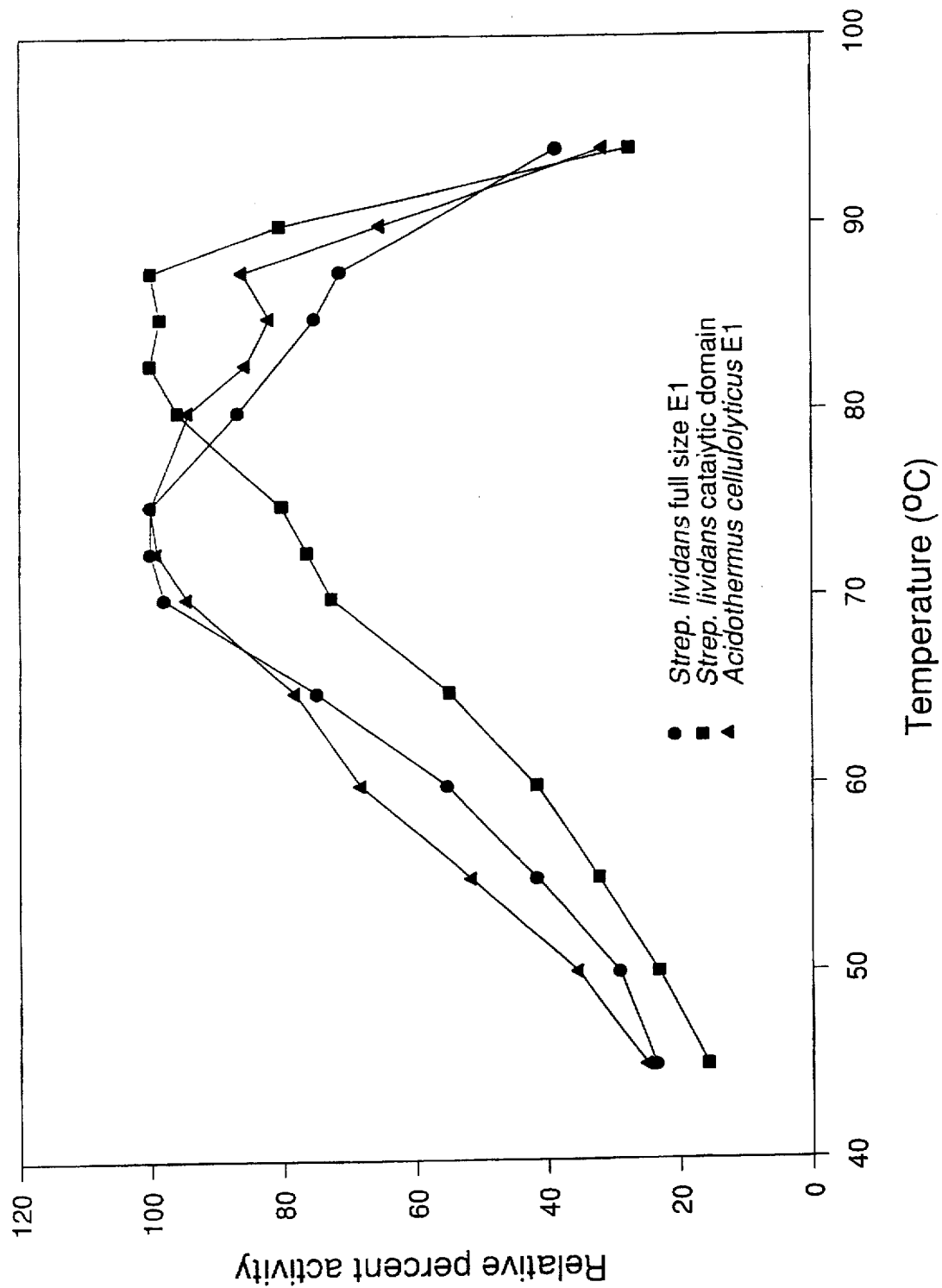
FIG. 3 compares the temperature optimum of the full size E1 enzyme to the temperature optimum of the catalytic domain of the E1 enzyme.

Comparison of the temperature optima of modified E1 and full size E1 was performed using 1 mg/mL p-nitrophenyl-g-D cellobioside substrate in 20 mM acetate, 100 mM NaCl, pH 5.0, at various temperatures with a 30 minute incubation time. See FIG. 3. The temperature optimum of the E1 CAT produced by papain cleavage is increased by 10° C. relative to the full size E1. Activity values in FIG. 3 are expressed as a percentage of the maximum activity detected.

It is further contemplated that one may include more than one catalytic domain in the hybrid enzyme. This may allow for a further increase in specific activity. Also, a catalytic domain containing cellulase activity other than endoglucanase activity may be included as well to reduce the number of cellulase enzymes one needs to add to a cellulosic substrate for polymer degradation.

EXAMPLE 3

Production of E1 CAT by Genetic Truncation of the Full Size E1 Coding Sequence

The amino acid sequence of E1 CAT is shown in FIG. 5. The entire amino acid sequence of pE1 CAT, including the C-terminus, is confirmed by the x-ray crystal structure derived from this molecule. An alternative to production of E1 CAT by papain cleavage of full size E1 is taught A molecular genetic approach was also developed to produce E1 CAT.

A strategy was desired to generate a genetically truncated E1 gene which would produce E1 CAT without requiring any downstream processing to achieve E1 CAT from a precursor molecule, as for papain cleavage. One way to accomplish this is to introduce a translational stop codon at or near the C-terminal residue of the catalytic domain.

Figure 7:
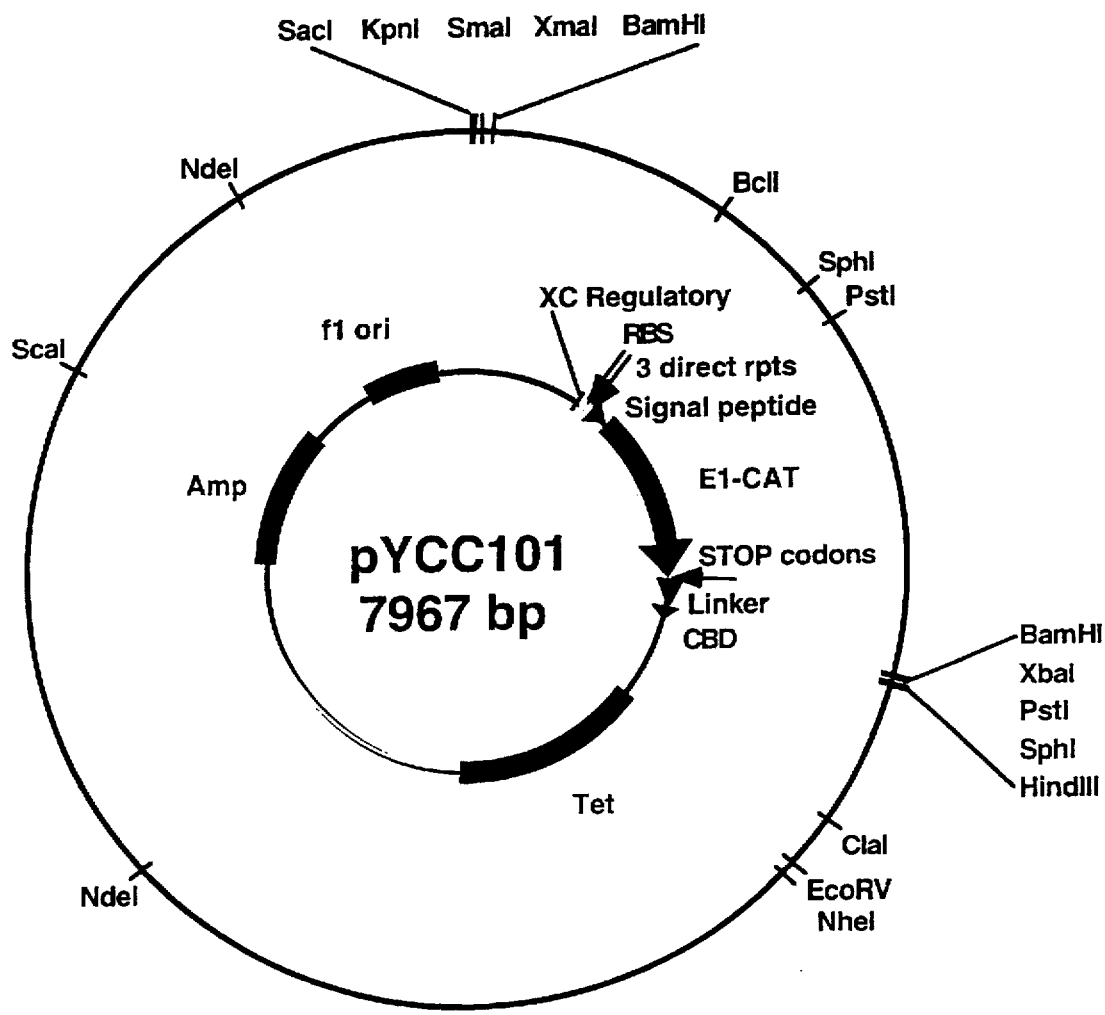
FIG. 7 is a plasmid map of pYCC101.

The 2.3 kb Bam H1 fragment containing most of the E1 gene was subcloned into pAlter-1 in preparation for site-directed mutagenesis (pYCC100). The nucleotide sequence for this fragment is shown in FIG. 6. A mutagenic 36-mer oligonucleotide (underlined in FIG. 6) was synthesized (5'-ATTTTCGATC CTGTCTAATG ATCTGCATCG CCTAGC-3')(SEQ ID NO:5). Using the Altered Sites® II kit (Promega Corp.) two consecutive codons immediately downstream of the C-terminal residue of E1-CAT (as determined by x-ray crystallography) were changed to different stop codons (TAA, TGA). The six mutagenic nucleotides are double-underlined in FIG. 6. The DNA sequence of this clone (pYCC101) has been confirmed by dideoxy DNA sequencing in the region of the site-directed mutations using the T7 Sequenase kit supplied by US Biochemical, (Cleveland, Ohio). A plasmid map of pYCC101 is shown in FIG. 7.

| | | | | | | | | | | | | | | |
|---|---|---|---|---|---|---|---|---|---|---|---|---|---|---|
| Native AA seq | S | S | I | F | D | P | V | G | A | S | A | S | P | S | S | Q | (SEQ ID NO: 6) |
| Native DNA seq | TCGTCGATTTTCGATCCTGTCGGCGCGTCTGCATCGCCTAGCAGTCAA (SEQ ID NO: 7) |
| Mutagenic oligo | ATTTTCGATCCTGTCTAATGATCTGCATCGCCTAGC (SEQ ID NO: 8) |
| Mutated DNA seq | TCGTCGATTTTCGATCCTGTCTAATGATCTGCATCGCCTAGCAGTCAA (SEQ ID NO: 9) |
| Mutated AA seq | S S I F D P V . . S A S P S S Q (SEQ ID NO: 10) |

Mutagenized DNA was transformed into E. coli strain ES1301. Transformants were screened for resistance to ampicillin and sensitivity to tetracycline in order to identify clones carrying the putatively mutagenized E1 gene. Many ampicillin-resistant candidate clones were subsequently screened on plates containing 1 mM 4-methylumbelliferyl-β-D-cellobioside (MUC) to verify expression of active E1. Plasmid DNA was prepared from several clones and employed as templates in dideoxy DNA sequencing reactions using the Sequenase® kit (U.S. Biochemical, Cleveland, Ohio) to verify the sequence of E1 DNA in the region of the intended mutation. The mutated sequence was detected in every clone which was sequenced. One of these clones was selected and designated pYCC101. Each of the successfully mutated clones expresses a protein not present in control cells and which migrates at a molecular weight of approximately 42 kDa in SDS-PAGE gels. This 42 kDa protein also reacts with a monoclonal antibody specific for the E1 endoglucanase on Western blots, thus confirming its identity as E1 CAT.

EXAMPLE 4

Differential Scanning Calorimetry (DSC)

Calorimetric studies of the denaturation of the full size E1 enzyme and the proteolytically cleaved E1 CAT were carried at pH 5.0 in 50 mM sodium acetate, using a Microcal MC-2 differential scanning microcalorimeter over a temperature range of 25°–95° C. and using a scan rate of 20° C./h. For the examples shown in FIG. 2, the protein concentrations were 0.24 mg/mL for the native E1 enzyme and 0.14 mg/mL for E1 CAT.

Figure 8:
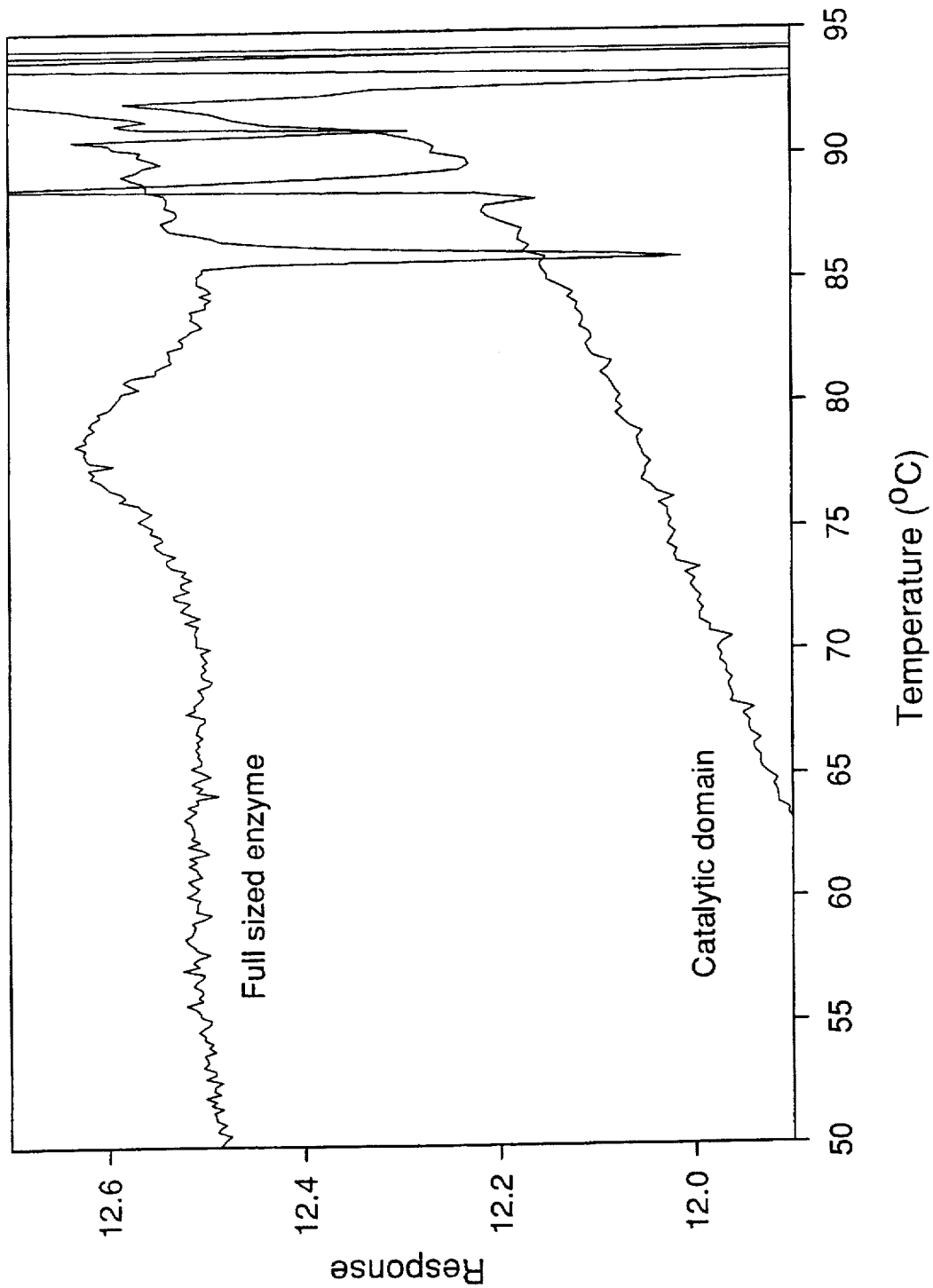
FIG. 8 is a DSC thermogram comparing the denaturation endotherm peak at 78° C. for the full size E1 and E1 CAT showing no peak below at least 88° C.

FIG. 8 shows the DSC thermogram for full size E1 enzyme displaying a prominent denaturation endotherm peak at approximately 78° C. This compares to the thermogram of E1 CAT, which shows no peak below at least 88° C. Since the thermograms are uninterpretable above 88° C. (limitation of the instrumentation), a reasonable conclusion is that the denaturation endotherm for the catalytic domain lies somewhere above 88° C.

EXAMPLE 5

Method for the Determination of the Functional Half-life of E1 and E1 CAT

The time at which half of the original endoglucanase activity remains following pre-incubation at 80° C. is referred to as its functional half-life. Enzymes were pre-incubated at 80° C. in 20 mM acetate, 100 mM NaCl, pH 5.0, in concentrations of 13.14 µg/mL for the full size enzyme E1 and 19.53 µg/mL for E1 CAT. Small aliquots (100 µL) from single tubes were removed at various times and assayed for activity by adding the 100 µL enzyme aliquot to 700 µL 20 mM acetate, 100 mM NaCl, pH 5.0, and 200 µL of 5 mg/mL p-nitrophenyl β-D cellobioside. The assay mixture was incubated at 65° C. for 30 minutes and the reaction stopped by adjusting the pH by addition of 2 mL of 1M $Na_2CO_3$. The activity was then measured by determining the concentration of the nitrophenolate anion, released as a result of catalytic activity of the enzyme, by measuring the absorbance at 410 nm of the quenched samples. Results shown in FIG. 2 demonstrate that E1 CAT has a functional half-life at 80° C. which nearly doubles that of full size E1 (16 h vs. 9 h).

Other options for generating genetically truncated E1 contemplated by the present inventors to be part of this invention include PCR of the coding sequence incorporating a non-homologous stop codon into the downstream synthetic primer; or using available restriction sites downstream of the DNA encoding the catalytic domain to delete the DNA sequences encoding the linker peptide and cellulose binding domain. Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials have been described.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

---

We claim:

1. A DNA having the nucleotide sequence of SEQ ID NO. 12.

2. The DNA according to claim 1, encoding the amino acid sequence of SEQ ID NO. 11.

3. A vector carrying the DNA according to claim 1 and a vector sequence encoding either an origin of replication or an integration site for a host genome.

4. The vector according to claim 3 further comprising DNA encoding a signal sequence operably linked thereto.

5. The vector according to claim 3 further comprising exogenous regulatory sequences capable of causing expression of said DNA in a suitable host; wherein a microorganism comprising *Pichia pastoris* contains the vector.

6. A DNA according to claim 1 encoding the catalytic domain of E1 endoglucanase.

7. A DNA according to claim 1 encoding the catalytic domain and the linker peptide of E1 endoglucanase.

8. The DNA according to claim 6 further comprising at least one domain from a cellulase gene other than E1 endoglucanase.

9. The DNA according to claim 7 wherein the DNA encodes a protein having an endoglucanase activity.

10. A microorganism containing the vector of claim 5.

11. A method for producing an endoglucanase having the amino acid sequence of claim 2, comprising enzymatic cleavage of the cellulose binding domain of full size E1 endoglucanase.

12. A method for producing an endoglucanase having the amino acid sequence of claim 2, comprising inserting at least one stop codon after the sequence encoding the catalytic domain of full size E1 endoglucanase so that the linker peptide and cellulose binding domain of E1 endoglucanase are not expressed in the expression product.

13. The DNA according to claim 2 wherein the DNA encodes a protein having an endoglucanase activity.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: E1-f primer ( x i ) SEQUENCE DESCRIPTION: SEQ ID NO: 1:

CTC GAG AAA AGA GCG GGC GGC GGC TAT TGG        30

( 2 ) INFORMATION FOR SEQ ID NO: 2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: Protein ( i x ) FEATURE:
        ( A ) NAME/KEY: E1-f primer ( x i ) SEQUENCE DESCRIPTION: SEQ ID NO: 2:

Leu Glu Lys Arg Ala Gly Gly Gly Tyr Trp
              5                      10

( 2 ) INFORMATION FOR SEQ ID NO: 3:

( i ) SEQUENCE CHARACTERISTICS:
        ( A ) LENGTH: 24 base pairs
        ( B ) TYPE: nucleic Acid
        ( C ) STRANDEDNESS: double
        ( D ) TOPOLOGY: linear ( i i ) MOLECULE TYPE: DNA ( i x ) FEATURE:
        ( A ) NAME/KEY: E1r ( x i ) SEQUENCE DESCRIPTION: SEQ ID NO: 3:

CCT AGG TTA ACT TGC TGC GCA GGC        24

( 2 ) INFORMATION FOR SEQ ID NO: 4:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: Protein ( i x ) FEATURE:
        ( A ) NAME/KEY: E1r ( x i ) SEQUENCE DESCRIPTION: SEQ ID NO: 4:

Ser Ala Ala Cys Ala
              5

( 2 ) INFORMATION FOR SEQ ID NO: 5:

( i ) SEQUENCE CHARACTERISTICS:
        ( A ) LENGTH: 36 base pairs
        ( B ) TYPE: nucleic Acid
        ( C ) STRANDEDNESS: double
        ( D ) TOPOLOGY: linear ( i i ) MOLECULE TYPE: DNA ( x i ) SEQUENCE DESCRIPTION: SEQ ID NO: 5:

ATTTTCGATC CTGTCTAATG ATCTGCATCG CCTAGC        36

( 2 ) INFORMATION FOR SEQ ID NO: 6:

( i ) SEQUENCE CHARACTERISTICS:
        ( A ) LENGTH: 16 amino acids
        ( B ) TYPE: amino acid ( C ) STRANDEDNESS: single
        ( D ) TOPOLOGY: linear ( i i ) MOLECULE TYPE: Protein ( x i ) SEQUENCE DESCRIPTION: SEQ ID NO: 6:

Ser  Ser  Ile  Phe  Asp  Pro  Val  Gly  Ala  Ser  Ala  Ser  Pro  Ser  Ser  Gln
               5                        10                       15

( 2 ) INFORMATION FOR SEQ ID NO: 7:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO: 7:

TCGTCGATTT TCGATCCTGT CGGCGCGTCT GCATCGCCTA GCAGTCAA          48

( 2 ) INFORMATION FOR SEQ ID NO: 8:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: mutagenic oligo ( x i ) SEQUENCE DESCRIPTION: SEQ ID NO: 8:

ATTTTCGATC CTGTCTAATG ATCTGCATCG CCTAGC          36

( 2 ) INFORMATION FOR SEQ ID NO: 9:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: mutated DNA ( x i ) SEQUENCE DESCRIPTION: SEQ ID NO: 9:

TCGTCGATTT TCGATCCTGT CTAATGATCT GCATCGCCTA GCAGTCAA          48

( 2 ) INFORMATION FOR SEQ ID NO: 10:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: Protein ( i x ) FEATURE:
        ( A ) NAME/KEY: Mutated amino acid ( x i ) SEQUENCE DESCRIPTION: SEQ ID NO: 10:

Ser  Ser  Ile  Phe  Asp  Pro  Val  Xaa  Xaa  Ser  Ala  Ser  Pro  Ser  Ser  Gln
               5                        10                       15

( 2 ) INFORMATION FOR SEQ ID NO: 11:

( i ) SEQUENCE CHARACTERISTICS:
        ( A ) LENGTH: 358 amino acids
        ( B ) TYPE: amino acid
        ( C ) STRANDEDNESS: single
        ( D ) TOPOLOGY: linear ( i i ) MOLECULE TYPE: Protein ( i x ) FEATURE:
        ( A ) NAME/KEY: E1-CAT ( x i ) SEQUENCE DESCRIPTION: SEQ ID NO: 11:

```
Ala Gly Gly Gly Tyr Trp His Thr Ser Gly Arg Glu Ile Leu Asp Ala
 1               5                  10                      15

Asn Asn Val Pro Val Arg Ile Ala Gly Ile Asn Trp Phe Gly Phe Glu
            20              25                  30

Thr Cys Asn Tyr Val Val His Gly Leu Trp Ser Arg Asp Tyr Arg Ser
        35              40                  45

Met Leu Asp Gln Ile Lys Ser Leu Gly Tyr Asn Thr Ile Arg Leu Pro
     50              55                  60

Tyr Ser Asp Asp Ile Leu Lys Pro Gly Thr Met Pro Asn Ser Ile Asn
 65                  70              75                      80

Phe Tyr Gln Met Asn Gln Asp Leu Gln Gly Leu Thr Ser Leu Gln Val
             85                  90                  95

Met Asp Lys Ile Val Ala Tyr Ala Gly Gln Ile Gly Leu Arg Ile Ile
            100             105                 110

Leu Asp Arg His Arg Pro Asp Cys Ser Gly Gln Ser Ala Leu Trp Tyr
        115             120                 125

Thr Ser Ser Val Ser Glu Ala Thr Trp Ile Ser Asp Leu Gln Ala Leu
    130             135                 140

Ala Gln Arg Tyr Lys Gly Asn Pro Thr Val Val Gly Phe Asp Leu His
145                 150                 155                 160

Asn Glu Pro His Asp Pro Ala Cys Trp Gly Cys Gly Asp Pro Ser Ile
            165                 170                 175

Asp Trp Arg Leu Ala Ala Glu Arg Ala Gly Asn Ala Val Leu Ser Val
            180                 185                 190

Asn Pro Asn Leu Leu Ile Phe Val Glu Gly Val Gln Ser Tyr Asn Gly
            195             200                 205

Asp Ser Tyr Trp Trp Gly Gly Asn Leu Gln Gly Ala Gly Gln Tyr Pro
    210             215                 220

Val Val Leu Asn Val Pro Asn Arg Leu Val Tyr Ser Ala His Asp Tyr
225                 230                 235                 240

Ala Thr Ser Val Tyr Pro Gln Thr Trp Phe Ser Asp Pro Thr Phe Pro
                245                 250                 255

Asn Asn Met Pro Gly Ile Trp Asn Lys Asn Trp Gly Tyr Leu Phe Asn
            260                 265                 270

Gln Asn Ile Ala Pro Val Trp Leu Gly Glu Phe Gly Thr Thr Leu Gln
        275                 280                 285

Ser Thr Thr Asp Gln Thr Trp Leu Lys Thr Leu Val Gln Tyr Leu Arg
    290                 295                 300

Pro Thr Ala Gln Tyr Gly Ala Asp Ser Phe Gln Trp Thr Phe Trp Ser
305                 310                 315                 320

Trp Asn Pro Asp Ser Gly Asp Thr Gly Gly Ile Leu Lys Asp Asp Trp
                325                 330                 335

Gln Thr Val Asp Thr Val Lys Asp Gly Tyr Leu Ala Pro Ile Lys Ser
```

Ser Ile Phe Asp Pro Val
355           358

( 2 ) INFORMATION FOR SEQ ID NO: 12:

( i ) SEQUENCE CHARACTERISTICS:
        ( A ) LENGTH: 2293 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: E1-CAT ( x i ) SEQUENCE DESCRIPTION: SEQ ID NO: 12:

| | | | | | |
|---|---|---|---|---|---|
| GGATCCACGT | TGTACAAGGT | CACCTGTCCG | TCGTTCTGGT | AGAGCGGCGG | GATGGTCACC | 60 |
| CGCACGATCT | CTCCTTTGTT | GATGTCGACG | GTCACGTGGT | TACGGTTTGC | CTCGGCCGCG | 120 |
| ATTTTCGCGC | TCGGGCTTGC | TCCGGCTGTC | GGGTTCGGTT | TGGCGTGGTG | TGCGGAGCAC | 180 |
| GCCGAGGCGA | TCCCAATGAG | GGCAAGGGCA | AGAGCGGAGC | CGATGGCACG | TCGGGTGGCC | 240 |
| GATGGGGTAC | GCCGATGGGG | CGTGGCGTCC | CCGCCGCGGA | CAGAACCGGA | TGCGGAATAG | 300 |
| GTCACGGTGC | GACATGTTGC | CGTACCGCGG | ACCCGGATGA | CAAGGGTGGG | TGCGCGGGTC | 360 |
| GCCTGTGAGC | TGCCGGCTGG | CGTCTGGATC | ATGGGAACGA | TCCCACCATT | CCCCGCAATC | 420 |
| GACGCGATCG | GGAGCAGGGC | GGCGCGAGCC | GGACCGTGTG | GTCGAGCCGG | ACGATTCGCC | 480 |
| CATACGGTGC | TGCAATGCCC | AGCGCCATGT | TGTCAATCCG | CCAAATGCAG | CAATGCACAC | 540 |
| ATGGACAGGG | ATTGTGACTC | TGAGTAATGA | TTGGATTGCC | TTCTTGCCGC | CTACGCGTTA | 600 |
| CGCAGAGTAG | GCGACTGTAT | GCGGTAGGTT | GGCGCTCCAG | CCGTGGGCTG | GACATGCCTG | 660 |
| CTGCGAACTC | TTGACACGTC | TGGTTGAACG | CGCAATACTC | CAACACCGA | TGGGATCGTT | 720 |
| CCCATAAGTT | TCCGTCTCAC | AACAGAATCG | GTGCGCCCTC | ATGATCAACG | TGAAAGGAGT | 780 |
| ACGGGGAGA | ACAGACGGGG | GAGAAACCAA | CGGGGATTG | GCGGTGCCGC | GCGCATTGCG | 840 |
| GCGAGTGCCT | GGCTCGCGGG | TGATGCTGCG | GGTCGGCGTC | GTCGTCGCGG | TGCTGGCATT | 900 |
| GGTTGCCGCA | CTCGCCAACC | TAGCCGTGCC | GCGGCCGGCT | CGCGCCGCGG | GCGGCGGCTA | 960 |
| TTGGCACACG | AGCGGCCGGG | AGATCCTGGA | CGCGAACAAC | GTGCCGGTAC | GGATCGCCGG | 1020 |
| CATCAACTGG | TTTGGGTTCG | AAACCTGCAA | TTACGTCGTG | CACGGTCTCT | GGTCACGCGA | 1080 |
| CTACCGCAGC | ATGCTCGACC | AGATAAAGTC | GCTCGGCTAC | AACACAATCC | GGCTGCCGTA | 1140 |
| CTCTGACGAC | ATTCTCAAGC | CGGGCACCAT | GCCGAACAGC | ATCAATTTTT | ACCAGATGAA | 1200 |
| TCAGGACCTG | CAGGGTCTGA | CGTCCTTGCA | GGTCATGGAC | AAAATCGTCG | CGTACGCCGG | 1260 |
| TCAGATCGGC | CTGCGCATCA | TTCTTGACCG | CCACCGACCG | GATTGCAGCG | GGCAGTCGGC | 1320 |
| GCTGTGGTAC | ACGAGCAGCG | TCTCGGAGGC | TACGTGGATT | TCCGACCTGC | AAGCGCTGGC | 1380 |
| GCAGCGCTAC | AAGGGAAACC | CGACGGTCGT | CGGCTTTGAC | TTGCACAACG | AGCCGCATGA | 1440 |
| CCCGGCCTGC | TGGGGCTGCG | GCGATCCGAG | CATCGACTGG | CGATTGGCCG | CCGAGCGGGC | 1500 |
| CGGAAACGCC | GTGCTCTCGG | TGAATCCGAA | CCTGCTCATT | TTCGTCGAAG | GTGTGCAGAG | 1560 |
| CTACAACGGA | GACTCCTACT | GGTGGGGCGG | CAACCTGCAA | GGAGCCGGCC | AGTACCCGGT | 1620 |
| CGTGCTGAAC | GTGCCGAACC | GCCTGGTGTA | CTCGGCGCAC | GACTACGCGA | CGAGCGTCTA | 1680 |
| CCCGCAGACG | TGGTTCAGCG | ATCCGACCTT | CCCCAACAAC | ATGCCCGGCA | TCTGGAACAA | 1740 |
| GAACTGGGGA | TACCTCTTCA | ATCAGAACAT | TGCACCGGTA | TGGCTGGGCG | AATTCGGTAC | 1800 |

| | | | | | |
|---|---|---|---|---|---|
| GACACTGCAA | TCCACGACCG | ACCAGACGTG | GCTGAAGACG | CTCGTCCAGT | ACCTACGGCC | 1860
| GACCGCGCAA | TACGGTGCGG | ACAGCTTCCA | GTGGACCTTC | TGGTCCTGGA | ACCCGATTC | 1920
| CGGCGACACA | GGAGGAATTC | TCAAGGATGA | CTGGCAGACG | GTCGACACAG | TAAAAGACGG | 1980
| CTATCTCGCG | CCGATCAAGT | CGTCGATTTT | CGATCCTGTC | TAATGATCTG | CATCGCCTAG | 2040
| CAGTCAACCG | TCCCCGTCGG | TGTCGCCGTC | TCCGTCGCCG | AGCCCGTCGG | CGAGTCGGAC | 2100
| GCCGACGCCT | ACTCCGACGC | CGACAGCCAG | CCCGACGCCA | ACGCTGACCC | CTACTGCTAC | 2160
| GCCCACGCCC | ACGGCAAGCC | CGACGCCGTC | ACCGACGGCA | GCCTCCGGAG | CCCGCTGCAC | 2220
| CGCGAGTTAC | CAGGTCAACA | GCGATTGGGG | CAATGGCTTC | ACGGTAACGG | TGGCCGTGAC | 2280
| AAATTCCGGA | TCC | | | | | 2293